United States Patent
Predick

(10) Patent No.: US 12,414,864 B2
(45) Date of Patent: Sep. 16, 2025

(54) TWO-PIECE SPINE IMPLANT INSTALLATION INSTRUMENT FOR USE WITH AN ENDOSCOPE AND METHOD OF USE

(71) Applicant: Life Spine, Inc., Huntley, IL (US)

(72) Inventor: Daniel P. Predick, Wheat Ridge, CO (US)

(73) Assignee: Life Spine, Inc., Huntley, IL (US)

( * ) Notice: Subject to any disclaimer, the term of this patent is extended or adjusted under 35 U.S.C. 154(b) by 389 days.

(21) Appl. No.: 18/098,642

(22) Filed: Jan. 18, 2023

(65) Prior Publication Data

US 2023/0225881 A1 Jul. 20, 2023

Related U.S. Application Data

(60) Provisional application No. 63/300,925, filed on Jan. 19, 2022.

(51) Int. Cl.
| | |
|---|---|
| A61F 2/46 | (2006.01) |
| A61B 1/00 | (2006.01) |
| A61B 1/313 | (2006.01) |
| A61F 2/44 | (2006.01) |

(52) U.S. Cl.
CPC ........ *A61F 2/4611* (2013.01); *A61B 1/00066* (2013.01); *A61B 1/00087* (2013.01); *A61B 1/3135* (2013.01); *A61F 2/4455* (2013.01); A61F 2002/4628 (2013.01); A61F 2002/4629 (2013.01)

(58) Field of Classification Search
CPC ........ A61F 2/46; A61F 2/4611; A61F 2/4603; A61B 17/7074
See application file for complete search history.

(56) References Cited

U.S. PATENT DOCUMENTS

| | | |
|---|---|---|
| 8,840,668 B1 | 9/2014 | Donahoe et al. |
| 2008/0306488 A1 | 12/2008 | Altarac et al. |
| 2012/0185045 A1* | 7/2012 | Morris .................. A61F 2/4611 606/86 A |
| 2019/0105183 A1 | 4/2019 | Adamo et al. |
| 2020/0352739 A1 | 11/2020 | Ouidja et al. |

FOREIGN PATENT DOCUMENTS

EP 2623069 A1 8/2013

* cited by examiner

*Primary Examiner* — Ellen C Hammond
(74) *Attorney, Agent, or Firm* — Bruce J. Bowman

(57) ABSTRACT

A two-piece medical instrument for installing an expandable interbody (intervertebral) spine implant via an endoscope, has a handle assembly and a shaft assembly configured for extension through the endoscope, the shaft assembly holding an expandable interbody spine implant when the shaft assembly is fully received by a head of the handle assembly, and releasing the spine implant upon retraction of the shaft assembly from the head of the handle assembly. The shaft assembly has a rod with a longitudinal bore and a sleeve situated on the rod that axially moves relative to the rod in response to the reception into and retraction from the handle assembly head, with the sleeve controlling capture and release of the implant by the rod. The distal end of the rod has a clamp formed by jaws that flex to capture and release the implant.

5 Claims, 10 Drawing Sheets

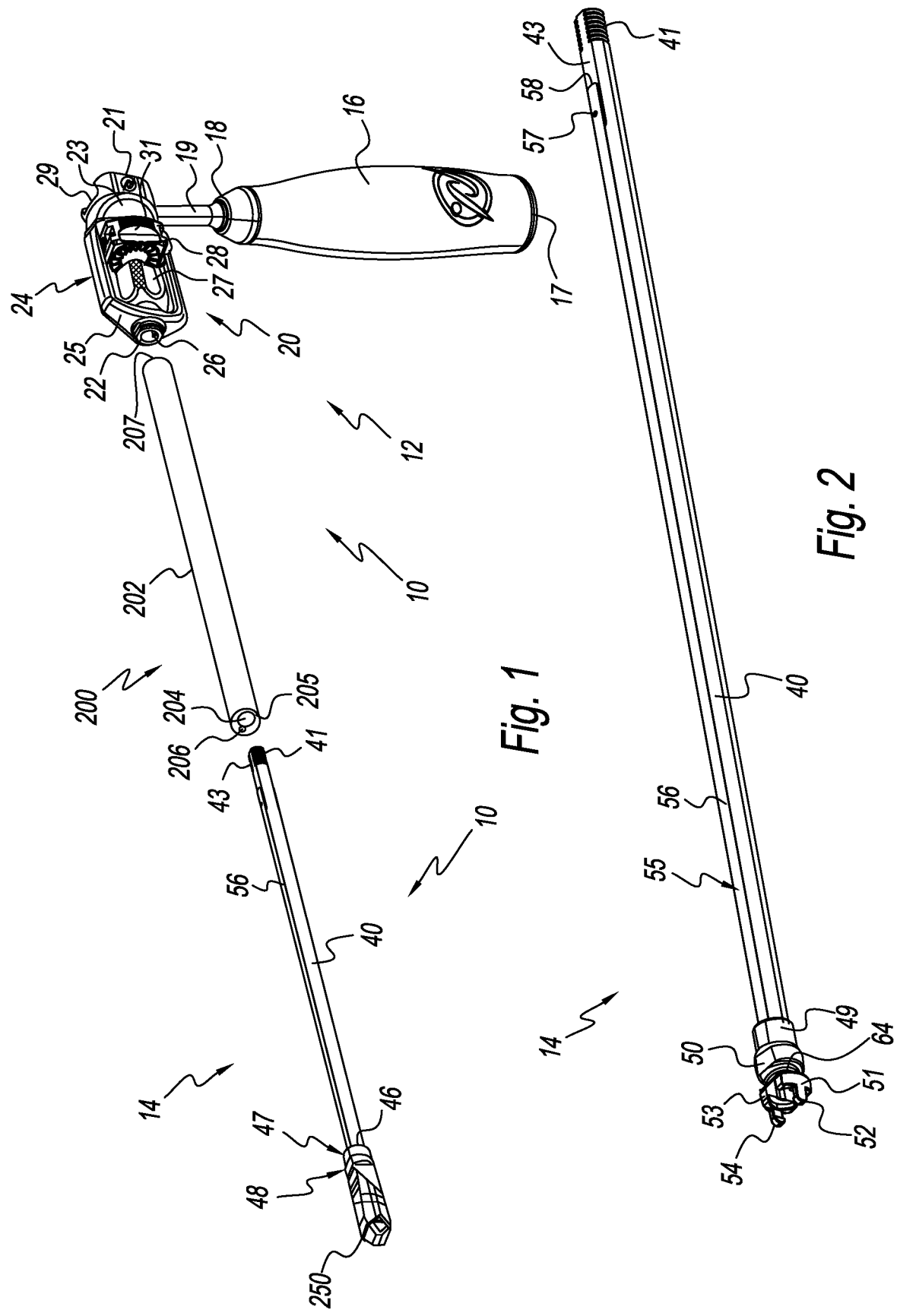

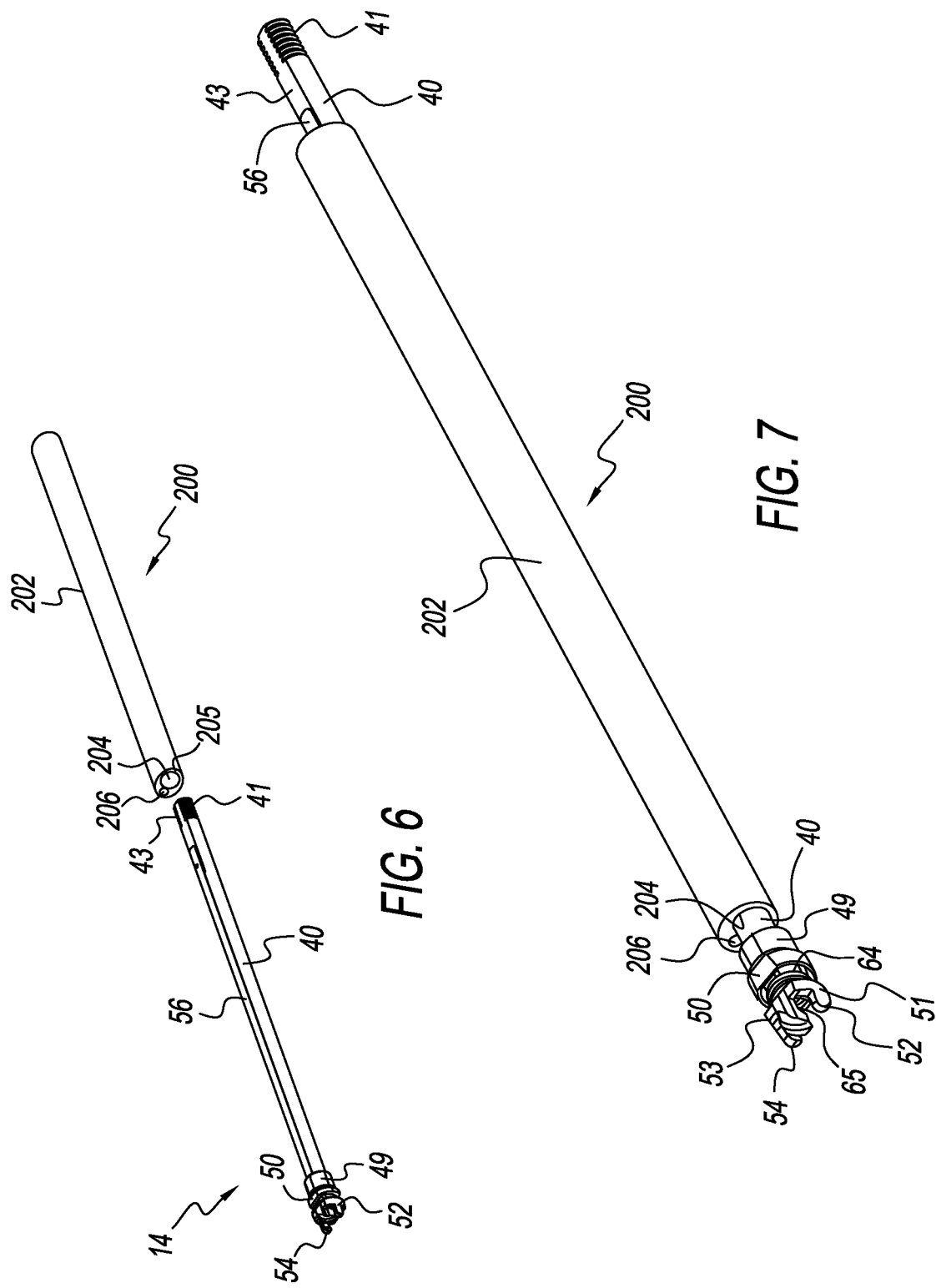

TWO-PIECE SPINE IMPLANT INSTALLATION INSTRUMENT FOR USE WITH AN ENDOSCOPE AND METHOD OF USE

CROSS-REFERENCE TO RELATED APPLICATIONS

This U.S. non-provisional utility patent application claims the benefit of and/or priority under 35 U.S.C. § 119(e) to U.S. provisional patent application Ser. No. 63/300,925 filed Jan. 19, 2022 titled "Two-Piece Spine Implant Installation Instrument For Use With An Endoscope And Method of Use," the entire contents of which is specifically incorporated herein by reference.

FIELD OF THE INVENTION

The present invention relates to methods and instruments for endoscopic spine surgery and, more particularly, to methods and instruments for endoscopically installing spine implants, such as but not limited to interbody spine implants, during a surgical spine procedure.

BACKGROUND OF THE INVENTION

Many people contend with spine issues due to age, disease, trauma, congenital, and acquired complications and conditions. While some spine issues can be alleviated without surgery, other spine issues necessitate surgery. Spine surgery may entail removing bone, tissue, and/or other material from a spine; replacing a portion or portions of a spine with one or more spine implants; affixing various spine hardware to the spine typically for stabilizing or providing fixation of one or more portions or elements of a spine; and/or installing a spine implant into and/or onto a spine.

It is important to minimize the amount of tissue injury, trauma, and post-operative pain to optimize a patient's recovery from spine surgery. Advances in spine surgery technology, equipment, instrumentation and procedures (collectively, spine surgery) over the years have resulted in significant improvement in lessening tissue injury, trauma, and post-operative pain. One advance was Minimally Invasive Surgery (MIS), where spinal surgical instruments and/or spine implants and other hardware are introduced into the body via cannulas that extend through a small incision in the body and positioned accordingly. Multiple cannulas with various surgical spine instruments are generally used. A currently foremost advance is Endoscopic Spine Surgery (ESS) that uses micro-sized incisions (less than 1-inch) and small tubular systems in combination with an endoscope to visualize the surgical field.

Particularly, ESS employs an endoscope to introduce a spine instrument and/or spine implant into the body and to perform a spine procedure using same. An endoscope is a slender, tubular optical instrument used as a viewing system for examining a body part with an associated spine instrument. With advances in optics, visualization of tissues, spinal imaging, and overall greater precision, endoscopic surgery is well suited for various spine procedures. One type of ESS may entail installing an implant between adjacent vertebrae of a spine (i.e., an intervertebral or interbody spine implant) as, for example, a substitute for a removed vertebral disc. The interbody spine implant installation instrument must provide for accurate placement, orientation, and possible deployment of an interbody spine implant within the constraints of an endoscope.

Current installation instruments for installing spine implants, such as but not limited to interbody spine implants, via an endoscope are wont in many respects. It would therefore be advantageous to have an instrument for installing a spine implants such as but not limited to interbody spine implants via an endoscope that addresses problems of prior art endoscopic spine implant installation instruments. It would furthermore be advantageous to have a method for installing spine implants such as but not limited to interbody spine implants via an endoscope.

The present two-piece spine implant installation instrument for use with an endoscope and methods of use addresses the above and more.

SUMMARY OF THE INVENTION

A medical instrument for installing a spine implant, such as, but not limited to, an expandable interbody or intervertebral spine implant, via an endoscope during a surgical spine procedure, utilizes a two-piece construction to deliver and insert the spine implant. The medical instrument or spine implant installer or installation tool is characterized by a first piece (handle assembly) and a second piece (shaft assembly) connectable to the handle assembly and sized for extension through the endoscope. The shaft assembly has a clamp at a distal end thereof that is configured to hold a preferably, but not necessarily, expandable interbody spine implant when a proximal end of the shaft assembly is fully received by a head of the handle assembly, and to release the expandable interbody spine implant upon retraction of the shaft assembly from the head of the handle assembly. Reception and retraction of the shaft assembly by the handle assembly is accomplished by manipulation of a rotatable knob of the head.

The shaft assembly has a rod with a longitudinal bore and a sleeve situated on the rod that axially moves relative to the rod in response to the reception of the rod (shaft assembly) into and retraction from the head of the handle assembly with the sleeve controlling capture and release of an expandable interbody implant by the clamp of the rod. The rod and sleeve share the same outer diameter.

The rod defines a proximal rod end and a distal rod end, with the proximal rod end having external threading and the distal rod end having the clamp formed by jaws that flex to capture and release the interbody spine implant. The sleeve has a distal sleeve end with a boss sized to receive the jaws of the distal end of the rod during reception of the rod into the handle assembly, and tangs that extend from the boss along the outside of the rod to near a proximal end of the sleeve. A spring about the jaws of the rod adjacent the boss aids in releasing the interbody spine implant from the clamp of the rod when the clamp emerges from the boss of the sleeve through axial movement of the rod.

The handle assembly has a handle portion defining a proximal handle portion end and a distal handle portion end with the head of the handle assembly connected to the proximal end, the head defined by a frame that includes an orifice and the rotatable knob which receives the proximal rod end. The proximal rod end of the rod of the shaft assembly is received into and removed from a nozzle of the frame that directs the proximal rod end into the rotatable knob.

In use, the portion of the installer that clasps onto the expandable interbody spine implant is fed up through the bottom of the cannulated endoscopic tube (endoscope) and engages with the handle assembly once fully inserted. As the threaded knob of the handle assembly is rotated, it draws the rod of the shaft assembly with its associated clasping jaws back into the handle assembly, while at the same time the tangs of the sleeve of the shaft assembly (on the rod of the shaft assembly) recede into the handle assembly and bottom out on flats within the handle assembly. This in turn causes the sleeve to compress the clasping jaws and lock onto the expandable interbody spine implant, all while being inserted through the endoscope. Once the expandable interbody spine implant has been inserted, the knob is rotated to back out the rod from the handle assembly, causing the spring to expand the jaws once the jaws emerge from the boss to release the expandable interbody spine implant.

Further aspects of the present invention will become apparent from consideration of the drawings and the following description of forms of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The present invention and its features, functions, and components will be better understood by reference to the accompanying drawings, wherein:

FIG. 1 is a front perspective view of an exemplary two-piece spine implant installation instrument (medical instrument), shown disassembled into a handle assembly and a shaft assembly, along with an endoscope, the shaft assembly holding an exemplary expandable interbody (intervertebral) spine implant;

FIG. 2 is a front perspective view of the shaft assembly of the present two-piece spine implant installation instrument;

FIG. 6 is a front perspective view of the shaft assembly of the present two-piece spine implant installation instrument along with the associated endoscope;

FIG. 7 is an enlarged front perspective view of the shaft assembly of the present two-piece spine implant installation instrument situated in and through the associated endoscope;

Figure 3:
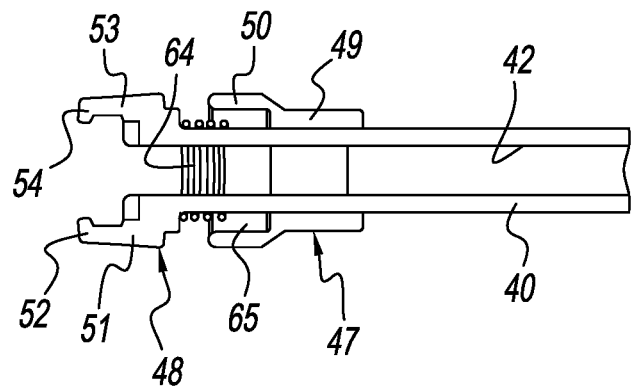
FIG. 3 is an enlarged side sectional view of a distal end of the shaft assembly of the present two-piece spine implant installation instrument.
Figure 4:
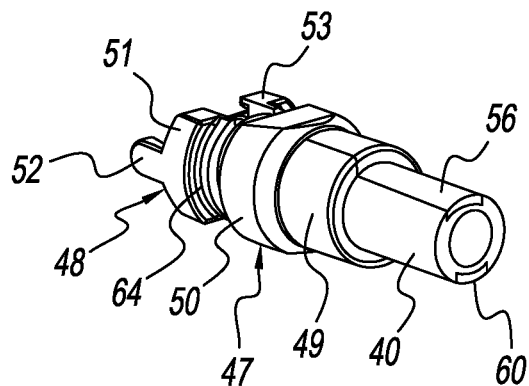
FIG. 4 is an enlarged rear view of the distal end of the shaft assembly of the present two-piece spine implant installation instrument.
Figure 5:
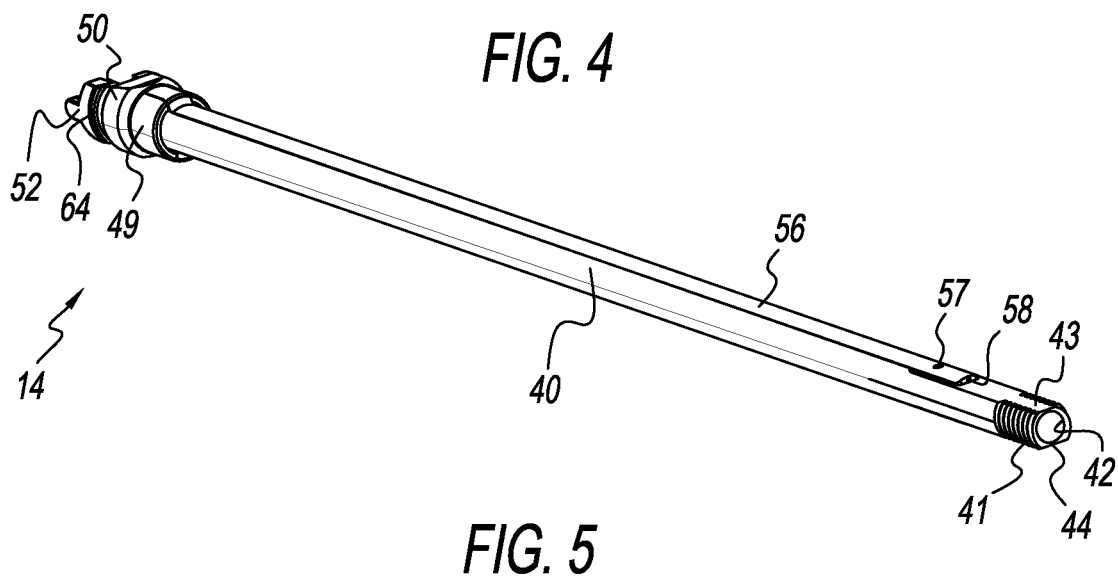
FIG. 5 is a rear perspective view of the shaft assembly of the present two-piece spine implant installation instrument.

For the purposes of promoting an understanding of the principles of the invention reference will now be made to the embodiment illustrated in the drawings and specific language will be used to describe the same. It will nevertheless be understood that no limitation of the scope of the invention is thereby intended. Any alterations and further modifications in the described embodiment, and any further applications of the principles of the invention as described herein are contemplated as would normally occur to one skilled in the art to which the invention relates.

DETAILED DESCRIPTION OF THE INVENTION

FIGS. 1-23 depict various views of the present two-piece interbody or intervertebral spine implant installation instrument (medical instrument), generally designated 10, and/or its constituent elements and components—including a handle assembly 12 and a shaft assembly 14, along with an exemplary endoscope 200 for which the two-piece intervertebral spine implant installation instrument 10 is designed to use. The endoscope 200 is representative of all types of endoscopes with which the two-piece interbody spine implant installation instrument 10 may be used. As is typical, the endoscope 200 has a tubular body 202 with a longitudinal bore 204 defining a distal endoscope end 205 and a proximal endoscope end 207, along with optics 206. The endoscope 200 may have other features and/or shapes not shown. The two-piece interbody spine implant installation instrument 10 is made from one or more surgical grade materials.

Figure 10:
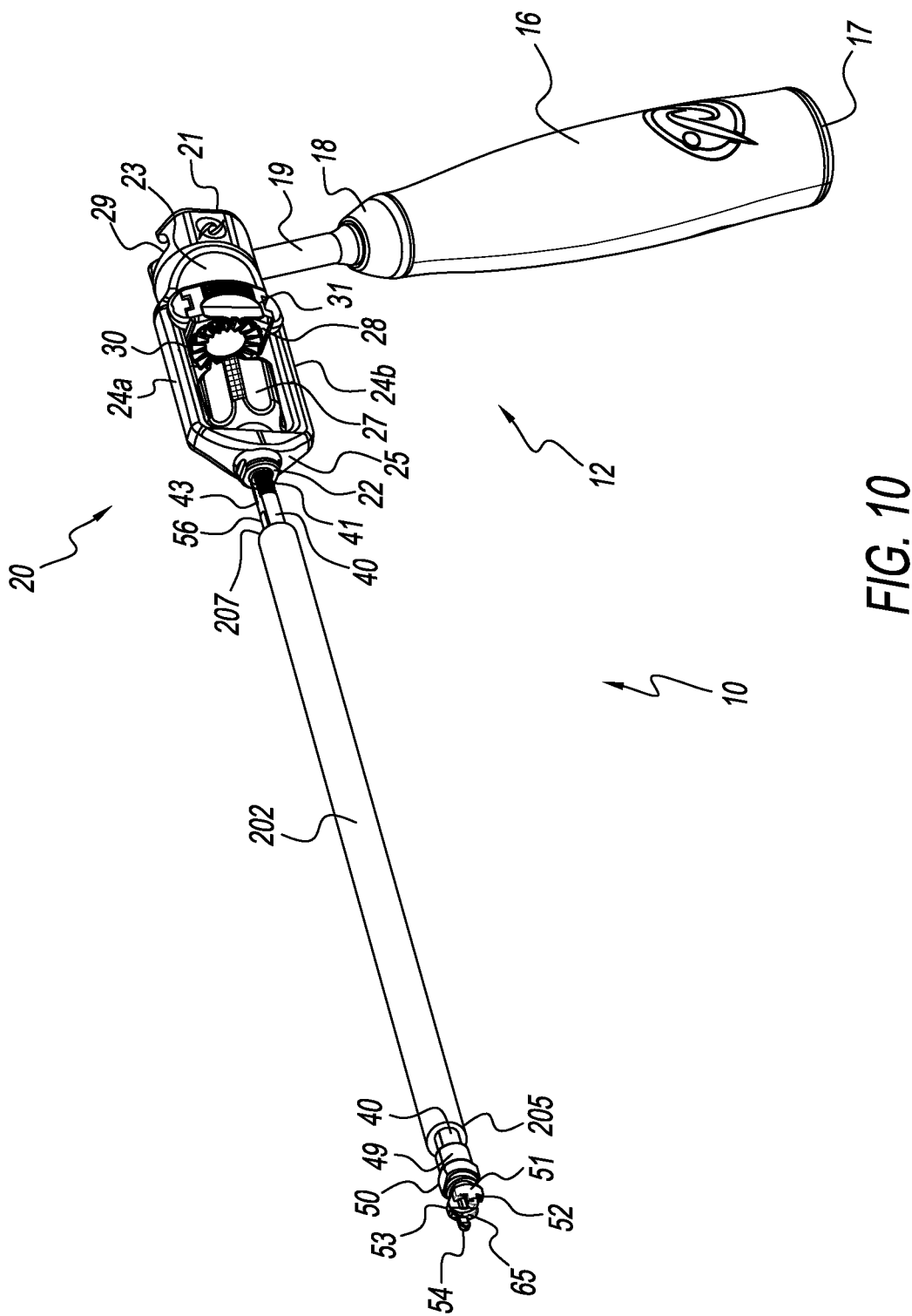
FIG. 10 is a front perspective view of the present two-piece spine implant instrument, shown assembled, along with the associated endoscope.

FIGS. 1 and 10 depict the two-piece interbody spine implant installation instrument 10, with FIG. 1 showing the two-piece interbody spine implant installation instrument 10 in an exploded view, and FIG. 10 showing the two-piece interbody spine implant installation instrument 10 assembled, both holding an exemplary expandable interbody spine implant 250 along with an endoscope 200. The exemplary expandable interbody spine implant 250 is representative of all types of interbody spine implants (expandable and non-expandable) as well as other spine implants. FIG. 2 depicts an enlarged view of the shaft assembly 14 of the two-piece interbody spine implant installation instrument 10. The shaft assembly 14 is characterized by a rod or the like 40 having a longitudinal bore 42, an externally threaded proximal end 41, and a distal end 46 with a clamp/clamp structure 48. A first flat 43 extends along the outside longitudinal length of the rod 40 (of which only a portion of the first flat 43 can be seen) that is proximate the externally threaded proximal end 41, while a second flat 44 (see, e.g., FIG. 5) extends along the outside longitudinal length of the rod 40 opposite the first flat 43, the nomenclature first and second being arbitrary. The first and second flats 43, 44 extend through the external threading of the proximal end 41. The distal clamp 48 of the rod 40 is defined, at least in part, by a first flange 51 having a first lip 52 that projects radially inward at the proximal end of the first flange 51/clamp 48, and a second flange 53 having a second lip 54 that projects radially inward at the proximal end of the second flange 53/clamp 48, the nomenclature first and second being arbitrary.

A sleeve 55 is disposed on and/or about the rod 40 for axial movement thereof relative to the rod 40. As best discerned in FIGS. 3-5, the distal end of the sleeve 55 has a boss 47 defined by a first collar 49 and a second collar 50 having a diameter larger that the first collar 49, the nomenclature first and second being arbitrary. The second collar 50 has a cavity or socket 65 that is sized to receive at least a rear portion or more of the clamp 48 of the rod 40 and, more particularly, the stepped rear (distal) ends of the first and second flanges 51, 53 of the clamp 48. The sleeve 55 also has a first tang 56 that extends along the first flat 43 of the rod 40 from the distal clamp 48 to a proximal end 58 thereof, and a second tang 60 that extends along the second flat 44 of the rod 40 from the distal clamp 48 to a proximal end 62 thereof. The first tang 56 has a bore 57 situated proximate the proximal end 58 of the first tang 56. The second tang 60 also has a bore 61 situated proximate the proximal end of the second tang 60. The rod 40 and sleeve 55 share the same outer diameter. This allows the shaft assembly 14 to fit through the endoscope and not be restricted in axial movement thereof on the rod 40. A spring or spring structure (spring) 64 is situated on and/or about a neck of the first and second flanges 51, 53. The spring 64 is formed to outwardly bias (spread out) the first and second flanges 51, 53 such that the clamp 48 is normally biased to release any implant and be ready to grasp an implant.

FIG. 6 depicts the shaft assembly 14 that is not holding an interbody spine implant ready to be inserted into the endoscope 200. FIG. 7 is an enlarged view of the shaft assembly 14 and endoscope 200 of FIG. 6 but with the shaft assembly 14 fully inserted into and through the endoscope 200. The assemblage (FIG. 7) is ready for reception by the handle assembly 12.

Figure 8:
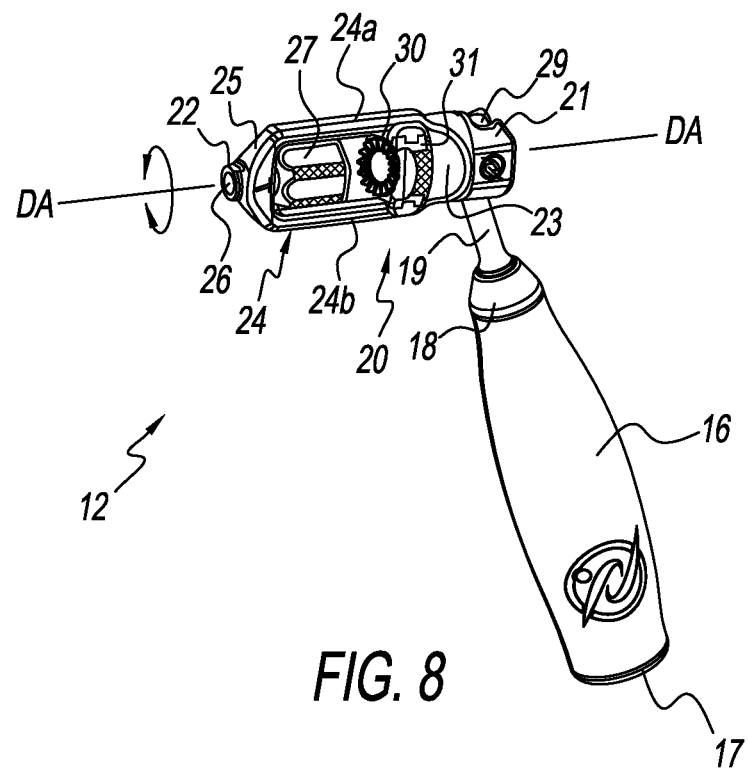
FIG. 8 is a front perspective view of the handle assembly of the present two-piece spine implant installation instrument.
Figure 9:
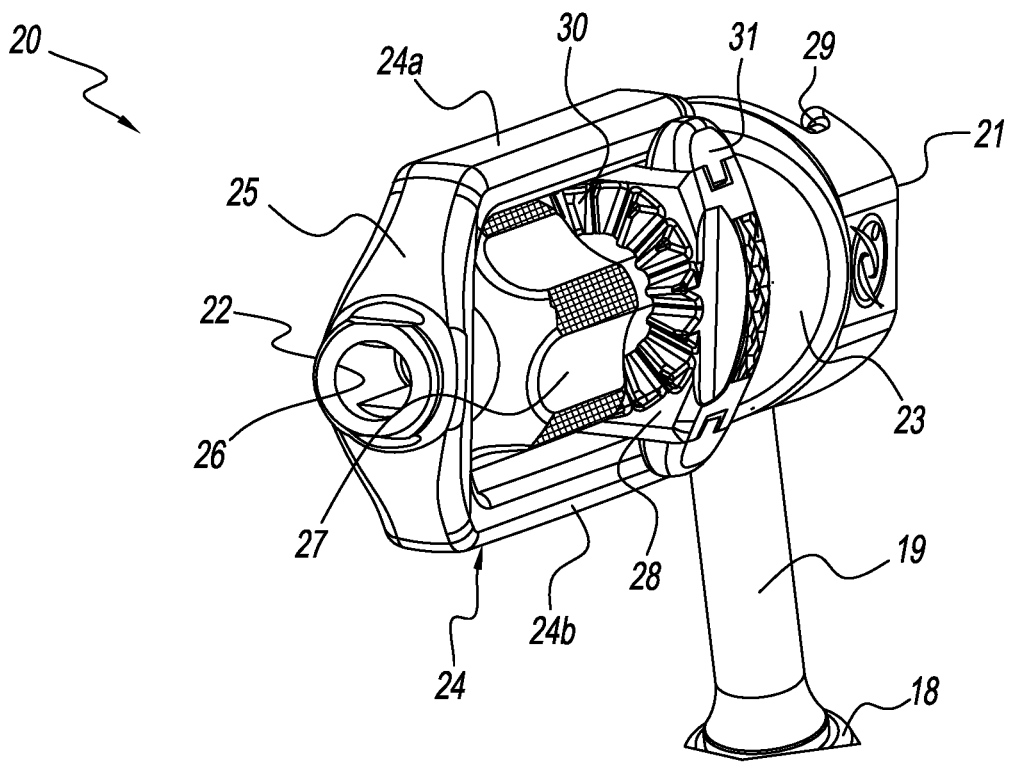
FIG. 9 is an enlarged front perspective view of the handle assembly of the present two-piece spine implant installation instrument.

Referring to FIGS. 8 and 9, the handle assembly 12 is shown. The handle assembly 12 has a handle 16 and a head 20. The handle 16 has a bottom (distal end) 17 and a top (proximal end 18), the handle 16 shaped to ergonomically fit a hand. A stem 19 extends from the top 18 that supports the head 20. The head 20 has a distal end 21 with a configured notch 29, and a proximal end 22. A neck 23 extends from the distal end 21 and supports a frame 24 having an upper frame portion 24a and a lower frame portion 24b, a nose 25, and a stop 28 opposite the nose 25. The stop 28 is part of first and second lateral rails 31, 32 that extend from and between the distal end of the upper and lower frame portions 24a, 24b that may be translatable on the upper and lower frame portions 24a, 24b in a direction co-axial with a drive axis DA of the head 20. The stop includes a ring of teeth/gearing 30. The head 20 is generally transverse to the handle 16 (see, e.g., FIGS. 1 and 8).

A knob 27 is situated in the frame 24 between the nose 25 and the stop 28. The knob 27 is rotatable within the upper frame portion 24a and the lower frame portion 24b (see, e.g., FIG. 18) and has an internally threaded bore 38 (see, e.g., FIGS. 12-14) that extends along the axis of rotation of the knob 27 (which is co-axial with the drive axis DA of the head 20, which is co-axial with the longitudinal axis LA of the shaft assembly 14) and through the knob 27. The internally threaded bore 38 is threaded and sized to receive the externally threaded proximal end 41 of the rod 40. The proximal end 22 of the head 20 has a generally round nozzle 26 (although other shapes may be used along with the shape of the rod 40) that provides an axial opening into the frame 24 and into the internally threaded bore 38 of the knob 27 so the knob 27 can receive the rod 40. A first flat 34 is provided in the outside of the nozzle 26 (see, e.g. FIGS. 11-14), while a second flat 35 is provided in the outside of the nozzle 26 (see, e.g. FIGS. 11-14), the nomenclature first and second being arbitrary. Rotation of the knob 27 in one direction draws the proximal end 41 of the rod 40 therein while rotation of the knob 27 in another opposite direction releases the proximal end 41 of the rod 40 from the knob 27.

Figure 11:
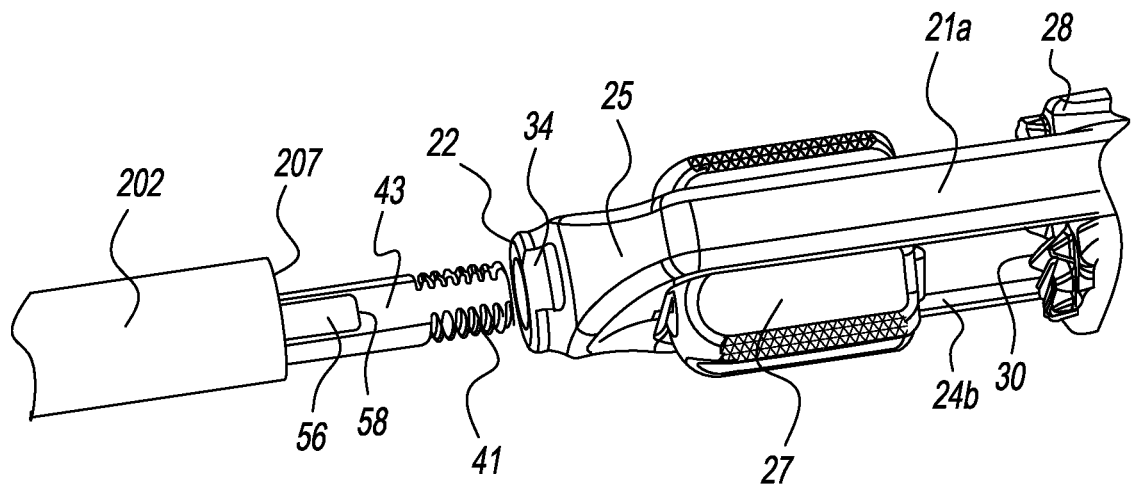
FIG. 11 is an enlarged perspective view of a distal end of the handle assembly of the present two-piece spine implant installation instrument and a proximal end of the shaft assembly of the present two-piece spine implant installation instrument extending from the associated endoscope and about to be received in the distal end of the handle assembly.
Figure 12:
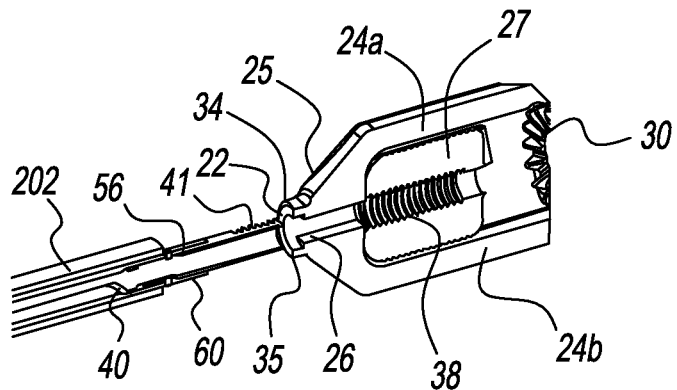
FIG. 12 is a sectional view along a longitudinal axis of the shaft assembly of the distal end of a head of the handle assembly of the present two-piece spine implant installation instrument and a proximal end of the shaft assembly of the present two-piece spine implant installation instrument extending from the associated endoscope and about to be received in the distal end of the head of the handle assembly.
Figure 13:
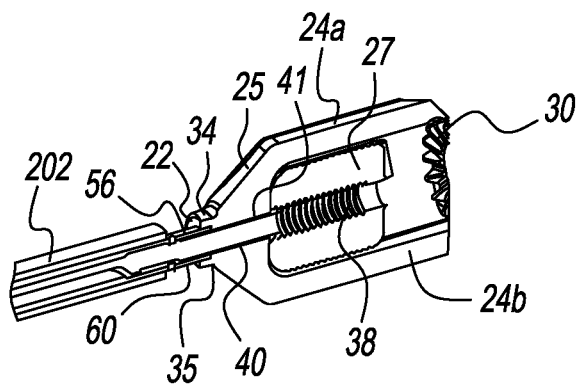
FIG. 13 is the sectional view of FIG. 12 showing the proximal end of the shaft assembly of the present two-piece spine implant installation instrument received into the distal end of the head of the handle assembly.
Figure 14:
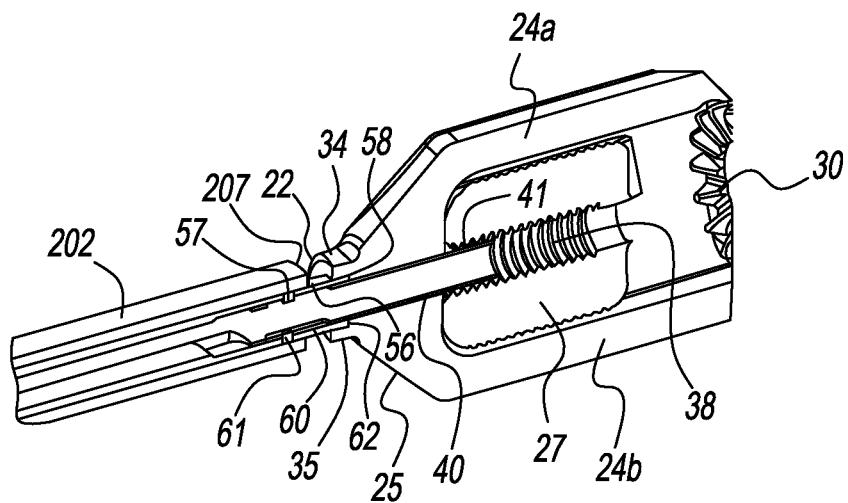
FIG. 14 is an enlarged view of the sectional view of FIG. 12 showing the proximal end of the shaft assembly of the present two-piece spine implant installation instrument received into the distal end of the head of the handle assembly.
Figure 23:
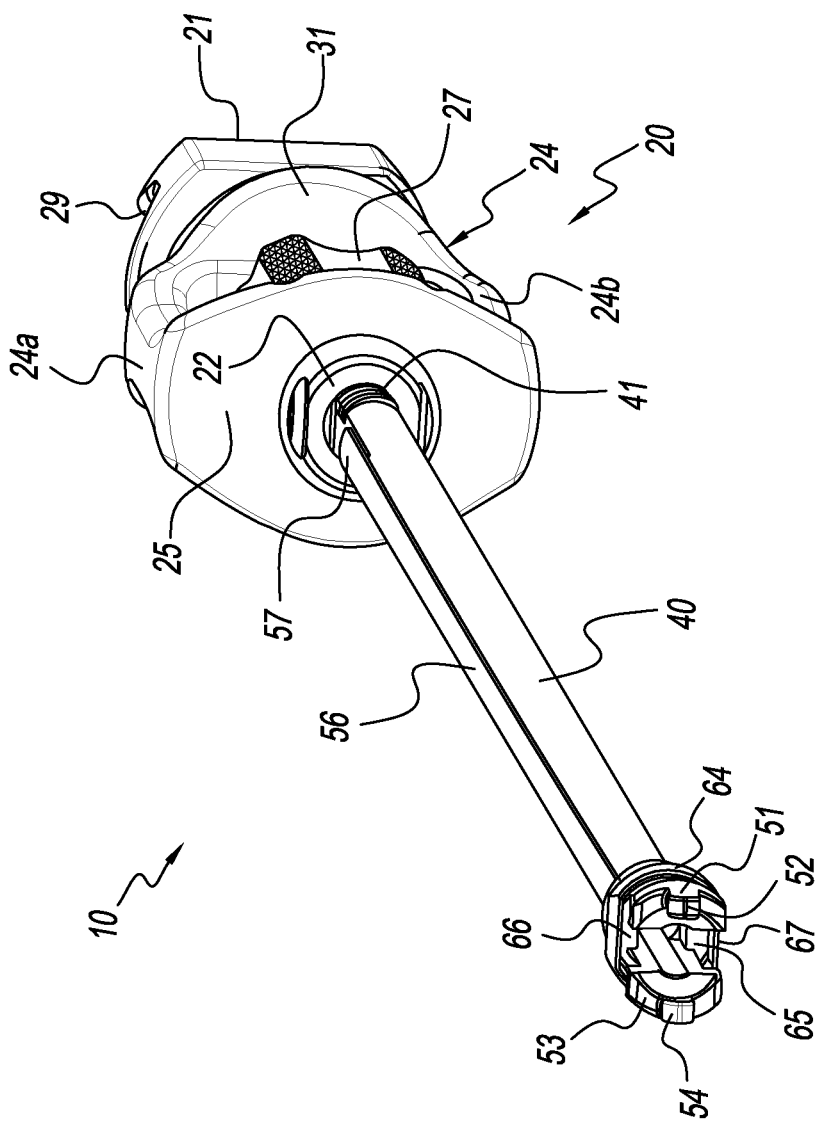
FIG. 23 is a front perspective view of the present two-piece spine installation instrument shown without the exemplary expandable interbody spine implant.

Reception of the shaft assembly 14 into the head 20 causes the clamp 48 of the shaft assembly 14 to close its jaws and grasp, hold or the like an interbody spine implant such as the exemplary expandable interbody spine implant 250 (see, e.g., FIGS. 15-16) by axially pulling the clamp 48 into the socket 65 of the boss 47 through mechanical restriction of axial translation of the sleeve on and relative to the rod 40 as the rod 40 axially translates. In FIG. 11, the threaded proximal end 41 of the rod 40 of the shaft assembly 14 is shown extending from the proximal end 207 of the endoscope 200 ready for reception into the distal end 22 (nozzle 26) of the head 20 in order for the clamp 48 to hold an implant. In FIG. 17, the threaded proximal end 41 of the rod 40 of the shaft assembly 14 has been initially received into the distal end 22 (nozzle 26) of the head 20. FIGS. 12-14 and 18 additionally depict the sequence of reception of the threaded proximal end 41 of the rod 40 from the endoscope body 202 and into the threaded bore 38 of the knob 27. In FIG. 12 the threaded proximal end 41 of the rod 40 is adjacent the nozzle bore 26 with the first tang 56 in the slot 43 of the rod 40 situated distal to the end 41, and the second tang 60 in the slot 44 of the rod 40 situated distal to the end 41. This is also seen in FIG. 23. In FIG. 13, the end 41 has been received into the nozzle 26 and is being introduced into the threaded bore 38 of the knob 27. Rotation of the knob 27 draws the rod end 41 axially into the threaded bore 38. As discerned in FIG. 13, the tangs 56 and 60 of the sleeve 55 are now adjacent the distal end 22 of the head 20. In FIGS. 14 and 18, the rod end 41 has been drawn further into the threaded bore 38 such that the end 58 of the first tang 56 of the sleeve 55 and the end 62 of the second tang 60 of the sleeve 55 both contact an annular ledge of the nozzle (see FIG. 18) which prevents further axial movement of the sleeve 55 on the rod 40 as the rod 40 is further axially moved into threaded bore 38 during further rotation of the knob 27 (in the same rotational direction).

Figure 15:
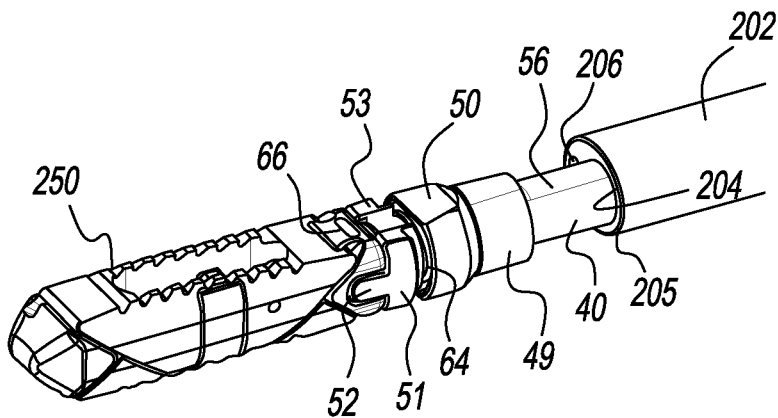
FIG. 15 is an enlarged perspective of the exemplary expandable interbody spine implant received on the distal end of the head of the handle assembly and extending from the associated endoscope.
Figure 16:
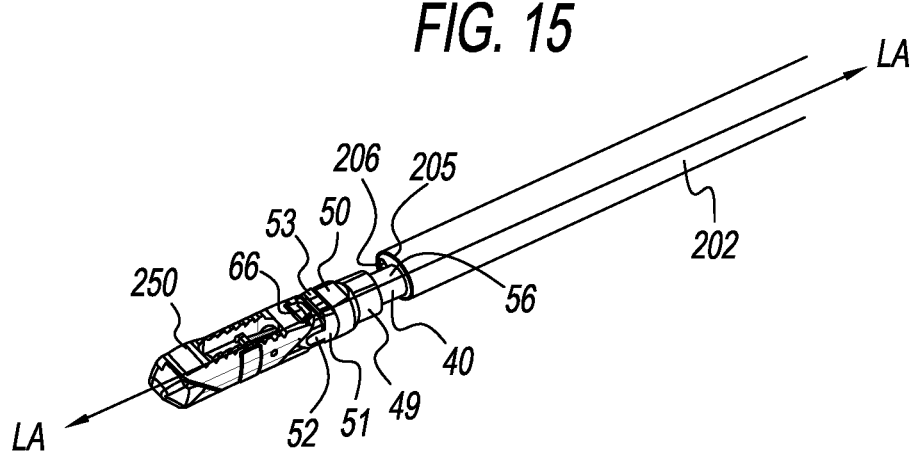
FIG. 16 is a reduced perspective view of the exemplary expandable interbody spine implant as received on the distal end of the head of the handle assembly and extending from the associated endoscope as depicted in FIG. 15 showing a longitudinal axis of the shaft assembly.
Figure 17:
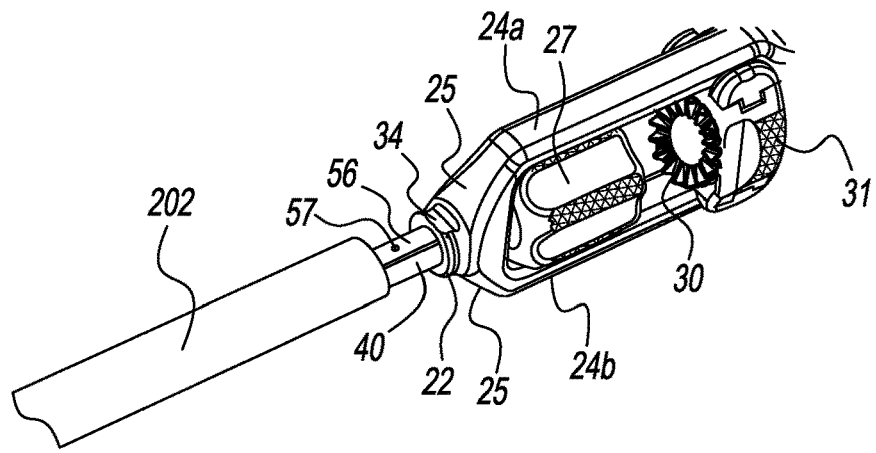
FIG. 17 is a perspective view of the distal end of the head of the handle assembly attached to the shaft assembly that extends from the associated endoscope.
Figure 18:
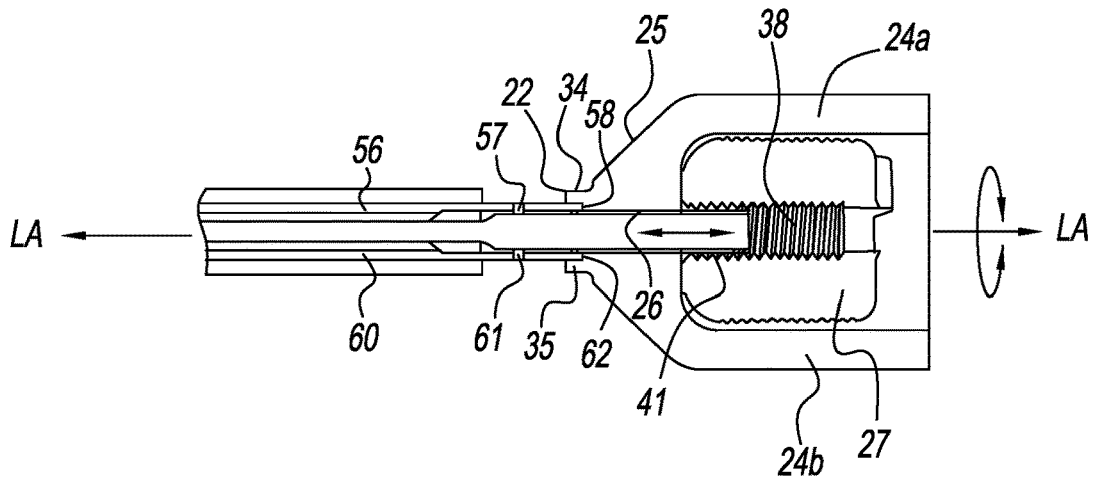
FIG. 18 is a sectional view along a longitudinal axis of the distal end of the head of the handle assembly, shaft assembly, and endoscope of FIG. 17 with the proximal end of the shaft assembly received by the head of the handle assembly, and a proximal end of a first shaft of the shaft assembly received in a control knob of the head of the handle assembly.
Figure 19:
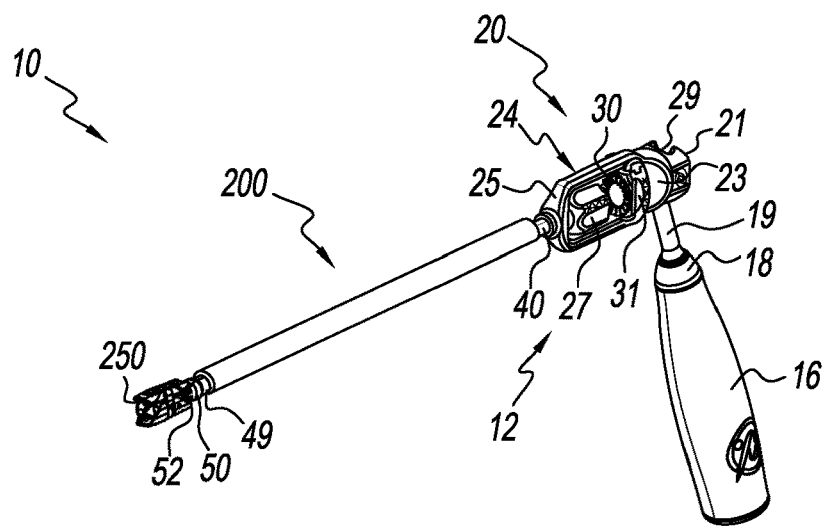
FIG. 19 is a reduced perspective view of the present two-piece spine implant installation instrument holding the exemplary expandable interbody spine implant and associated endoscope.
Figure 20:
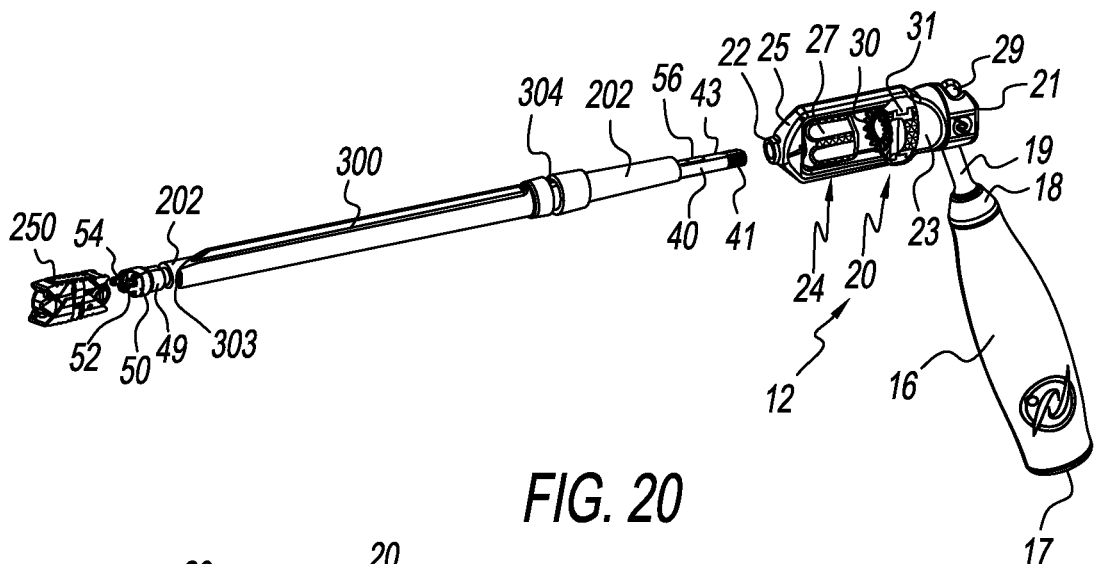
FIG. 20 is the reduced perspective view of the present two-piece spine implant installation instrument of FIG. 19 with the endoscope and shaft assembly shown exploded from the handle assembly and the exemplary expandable interbody spine implant.
Figure 21:
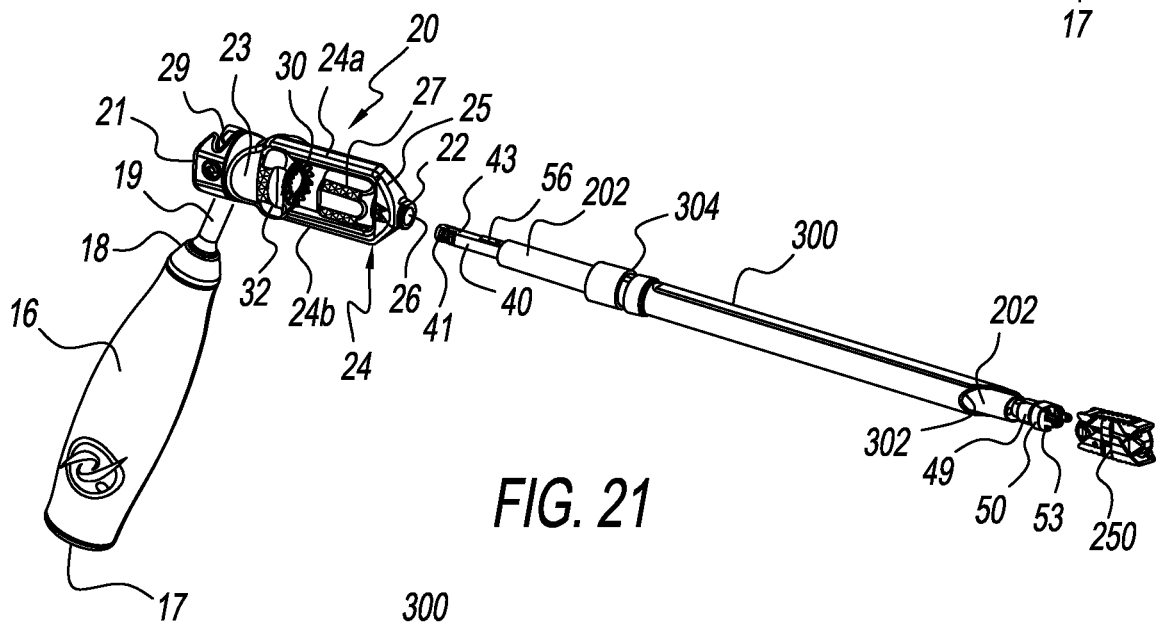
FIG. 21 is a reduced perspective view of the present two-piece spine implant installation instrument from a side opposite that shown in FIG. 20.
Figure 22:
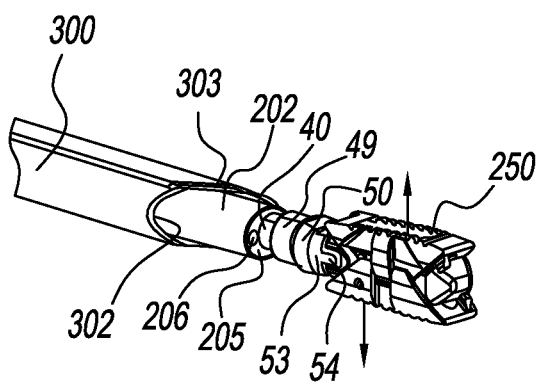
FIG. 22 is a perspective view of the distal end of the present two-piece spine implant installation instrument with the exemplary expandable interbody spine implant received by a clamp of the distal end of the shaft assembly.

The clamp 48 is configured to receive and hold an interbody spine implant, such as the exemplary expandable interbody spine implant 250, as the clamp 48 is axially drawn into the boss socket 65 upon longitudinally axial movement of the rod 40 (along the longitudinal axis LA of the rod 40—see, e.g., FIGS. 16 and 18) relative to the sleeve 55, due to the sleeve being stopped from further axial movement by the ends 58, 62 of the sleeve tangs 56, 60 abutting the internal annular ring of the nozzle 26 (as sequenced in FIGS. 11-18). The rod 40, however, can still advance in the threaded knob bore 38 (see, e.g., FIG. 17). As the rod 40 advances further into the knob bore 38 through further knob rotation, the first and second flanges 51, 53 are pulled axially into the boss socket 65 where, against the bias of the spring 64, the first and second flanges 51, 53 are forced to flex radially inward, thereby grasping an implant (see, e.g., FIGS. 15, 16). Both FIGS. 15-17 depict a position wherein the rod 40 has been fully drawn into the knob 27, the clamp 48 is securely holding the implant 250, and the clamp 48 has been fully pulled into the socket 65 of the boss 50.

Referring additionally to FIGS. 19-22, a method of use of the present two-piece interbody spine implant installation instrument 10 in conjunction with an endoscope can be discerned and herein described. Other methods and/or sequences are contemplated. In use, the portion of the installer that clasps onto the expandable interbody spine implant (e.g., clamp 48) is fed up through the bottom of the cannulated endoscopic tube (e.g., endoscope 200) and engages with the handle assembly (e.g., handle assembly 12) once fully inserted. As the threaded knob (e.g., knob 27) of the handle assembly is rotated, it draws the rod (e.g., rod 40) of the shaft assembly (e.g., shaft assembly 14) with its associated clasping jaws (e.g., jaws 51, 53) back into the handle assembly, while at the same time the tangs (e.g., tangs 56, 60) of the sleeve (e.g., sleeve 55) of the shaft assembly (on the rod of the shaft assembly) recede into the handle assembly and bottom out on flats within the handle assembly. This in turn causes the sleeve to compress the clasping jaws and lock onto the expandable interbody spine implant (e.g., implant 250), all while being inserted through the endoscope. Once the expandable interbody spine implant has been inserted, the knob is rotated to back out the rod from the handle assembly, causing the spring to expand the jaws once the jaws emerge from the boss to release the expandable interbody spine implant.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected. It should be understood that while the use of words such as preferable, preferably, preferred or more preferred utilized in the description above indicate that the feature so described may be more desirable, it nonetheless may not be necessary and embodiments lacking the same may be contemplated as within the scope of the invention.

What is claimed is:

1. A medical instrument for placing an interbody spine implant in an intervertebral space of a spine with the use of an endoscope, the medical instrument comprising:
   a first part including a handle, a head on the handle, an orifice in the head, and a rotatable knob situated in the head, the rotatable knob having an internally threaded bore axially aligned with the orifice;
   a second part operably connectable to the head on the handle and configured for receipt through an endoscope, the second part including a rod with a longitudinal bore and defining a distal rod end and a proximal rod end with the proximal rod end having external threading, a clamp at the distal rod end and configured to hold an intervertebral spine implant when the externally threaded proximal rod end is fully threaded into the internally threaded bore of the rotatable knob of the head and through the orifice of the head on the handle, and to release the intervertebral spine implant upon unthreading of the externally threaded proximal rod end from the internally threaded bore of the rotatable knob of the head on the handle, and a sleeve situated on the rod that axially moves relative to the rod in response to threaded reception into and unthreaded retraction from the rotatable knob of the head of the handle, wherein the clamp is formed by jaws that flex to capture and release the intervertebral spine implant, wherein the clamp is formed by jaws that flex to capture and release the intervertebral spine implant;
   the sleeve defining a distal sleeve end with a boss sized to receive the jaws of the distal rod end during threaded reception of the externally threaded proximal end of the rod into the orifice of the head, and a proximal sleeve end, and tangs that extend from the boss along an outside of the rod to near the proximal sleeve end; and
   a spring about the jaws of the rod adjacent the boss to aid in releasing the intervertebral spine implant from the clamp of the rod when the clamp emerges from the boss of the sleeve through axial movement of the rod.

2. The medical instrument of claim 1, wherein the handle defines a proximal handle end and a distal handle end with the head of the handle connected to the proximal handle end, the head defined by a frame that includes the orifice and the rotatable knob.

3. The medical instrument of claim 2, wherein the jaws comprise a first jaw portion and a second jaw portion.

4. The medical instrument of claim 3, wherein the handle is disposed perpendicular to the head.

5. The medical instrument of claim 4, wherein the head is connected to the proximal handle end via a neck.

* * * * *